US011083405B1

(12) United States Patent
Lacy et al.

(10) Patent No.: US 11,083,405 B1
(45) Date of Patent: Aug. 10, 2021

(54) SYSTEMS AND METHODS FOR SCREENING SUBJECTS BASED ON PUPILLARY RESPONSE TO OLFACTORY STIMULATION

(71) Applicant: Great Plain Technologies LLC, Pittston, PA (US)

(72) Inventors: Clifton R. Lacy, Highland Park, NJ (US); Warren S. Gifford, Monroe Township, NJ (US); David L. Turock, Fort Lauderdale, FL (US)

(73) Assignee: GREAT PLAIN TECHNOLOGIES LLC, Pittston, PA (US)

( * ) Notice: Subject to any disclaimer, the term of this patent is extended or adjusted under 35 U.S.C. 154(b) by 0 days.

(21) Appl. No.: 17/167,728

(22) Filed: Feb. 4, 2021

(51) Int. Cl.
*A61B 5/00* (2006.01)
*A61B 5/16* (2006.01)

(52) U.S. Cl.
CPC .......... *A61B 5/4011* (2013.01); *A61B 5/163* (2017.08); *A61B 5/746* (2013.01)

(58) Field of Classification Search
CPC ........ A61B 5/4011; A61B 5/163; A61B 5/746
See application file for complete search history.

(56) References Cited

U.S. PATENT DOCUMENTS

| | | | | |
|---|---|---|---|---|
| 10,888,283 | B1 * | 1/2021 | Benjauthrit | A61B 8/08 |
| 2012/0078065 | A1 * | 3/2012 | De Lemos | A61M 16/021 |
| | | | | 600/301 |

OTHER PUBLICATIONS

Hornuss D, Lange B, Schroter N, Rieg S, Kern WV, Wagner D. Anosmia in COVID-19 patients. Clin Microbiol Infect. 2020;26(10): 1426-1427. doi:10.1016/j.cmi.2020.05.017 (Year: 2020).*
Nadia Aguillon-Hernandez, et al. "An odor identification approach based on event-related pupil dilation and gaze focus," International Journal of Psychophysiology, vol. 96, Issue 3, 2015, pp. 201-209, https://doi.org/10.1016/j.ijpsycho.2015.03.009 (Year: 2015).*

(Continued)

*Primary Examiner* — Eric J Messersmith
(74) *Attorney, Agent, or Firm* — Troutman Pepper Hamilton Sanders LLP

(57) ABSTRACT

A system and method for screening a subject for a pupillary response to an olfactory stimulus as an indication for COVID-19. The method can include providing the olfactory stimulus to the subject via a scent dispenser, measuring a pupillary response of the subject to the olfactory stimulus via a detector, and comparing the measured pupillary response to a reference. The reference could include a default value or a characterized pupillary response for the subject or a population of individuals to the olfactory stimulus. The method can further include determining whether the subject demonstrates a diminished or an absent response to the olfactory stimulus according to whether the measured pupillary response differs from the reference by a threshold and providing an alert accordingly. The alert can include an intervention associated with COVID-19, such a recommendation to seek medical evaluation or take a COVID-19 diagnostic test.

19 Claims, 8 Drawing Sheets

(56) References Cited

OTHER PUBLICATIONS

Hummel T, Rosenheim K, Konnerth C-G, Kobal G. Screening of Olfactory Function with a Four-Minute Odor Identification Test: Reliability, Normative Data, and Investigations in Patients with Olfactory Loss. Annals of Otology, Rhinology & Laryngology. 2001; 110(10):976-981. doi:10.1177/000348940111001015 (Year: 2001).*

Schneider, et al., "Pupillary responses to intranasal trigeminal and olfactory stimulation," J Neural Transm (2009) 116:885-889 DOI 10.1007/s00702-009-0244-7 (Year: 2009).*

Nguyen, et al., "Olfactory exploration: State of the art," European Annals of Otorhinolaryngology, Head and Neck diseases 133 (2016) 113-118 (Year: 2016).*

* cited by examiner

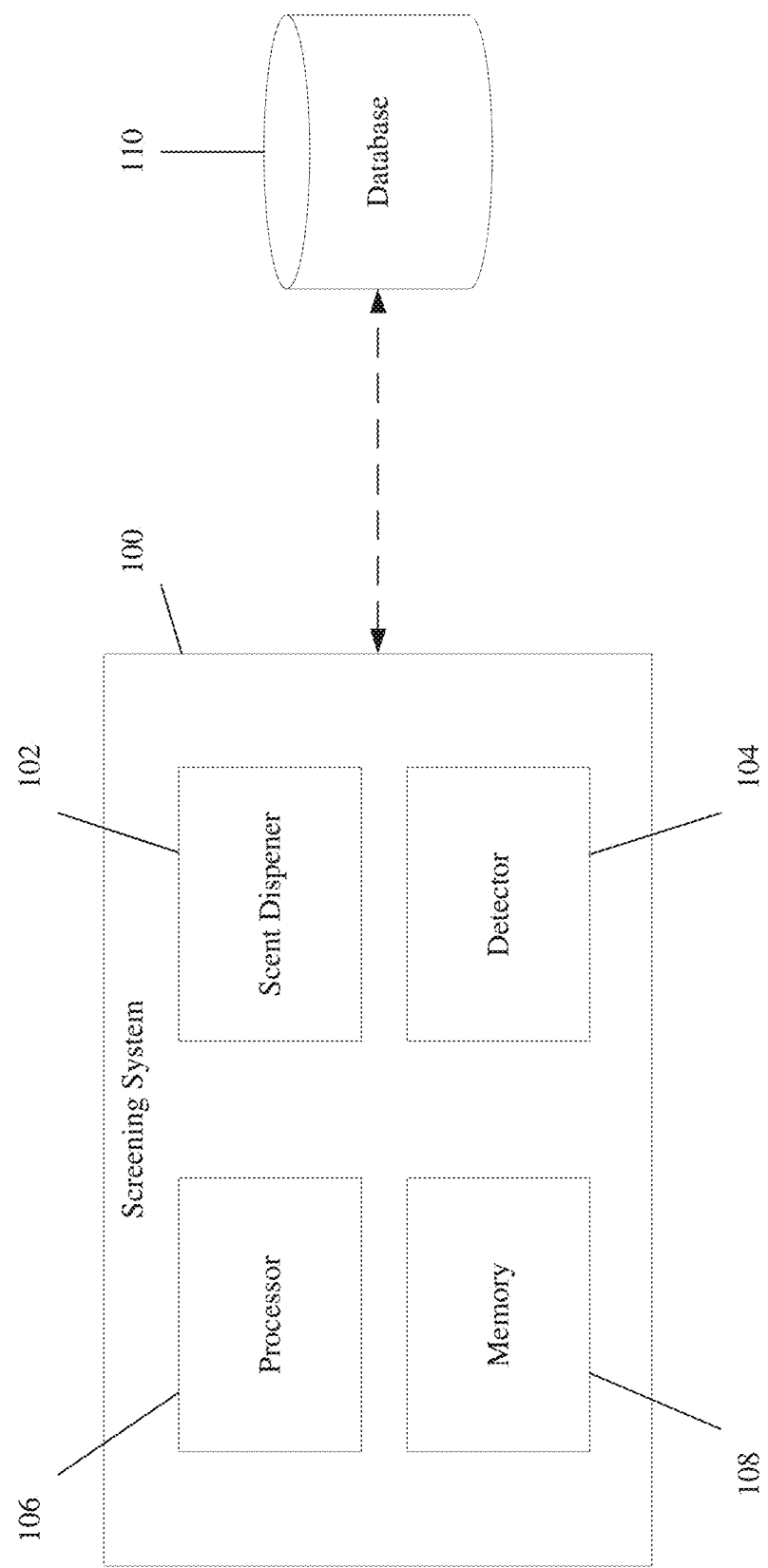

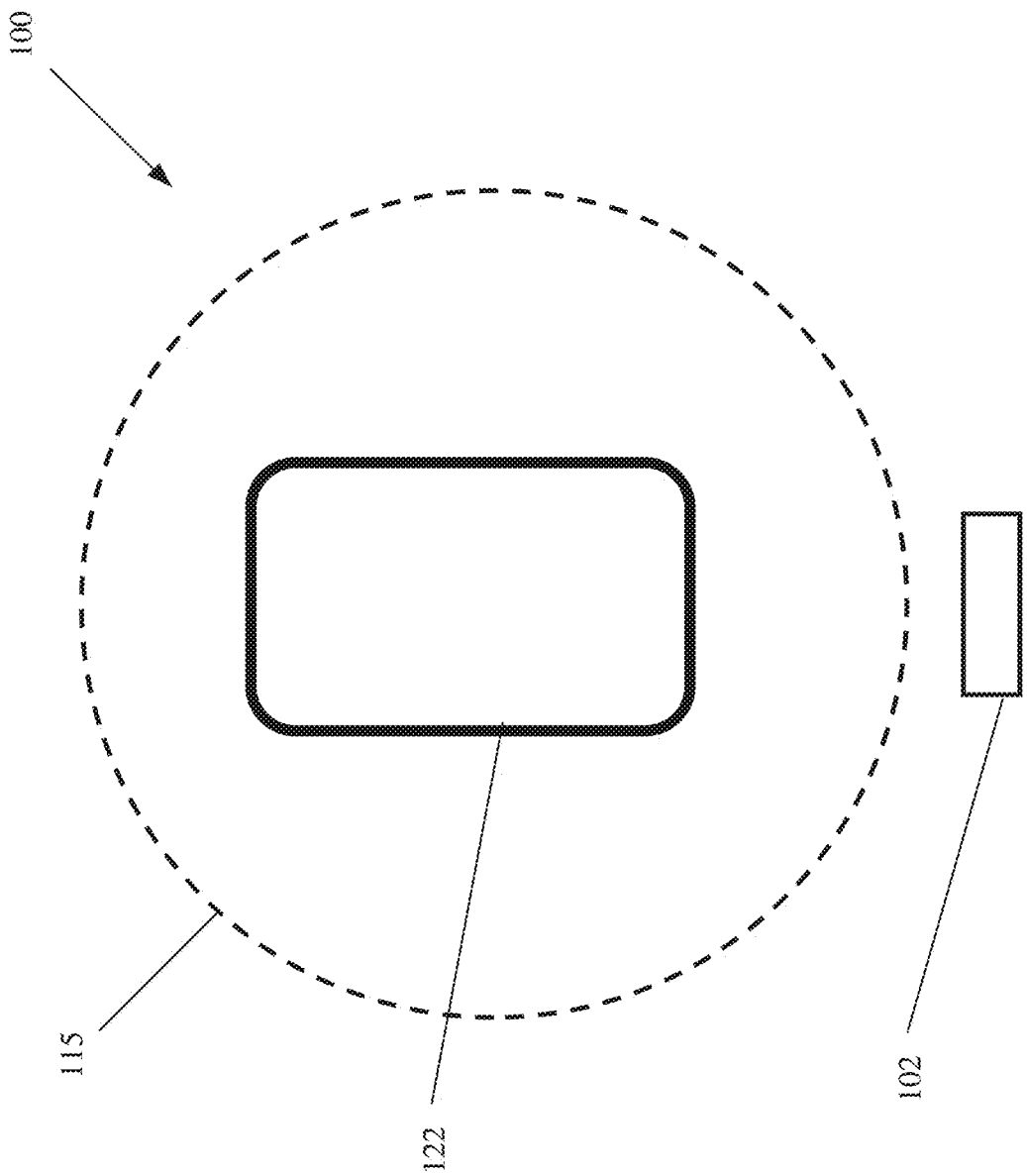

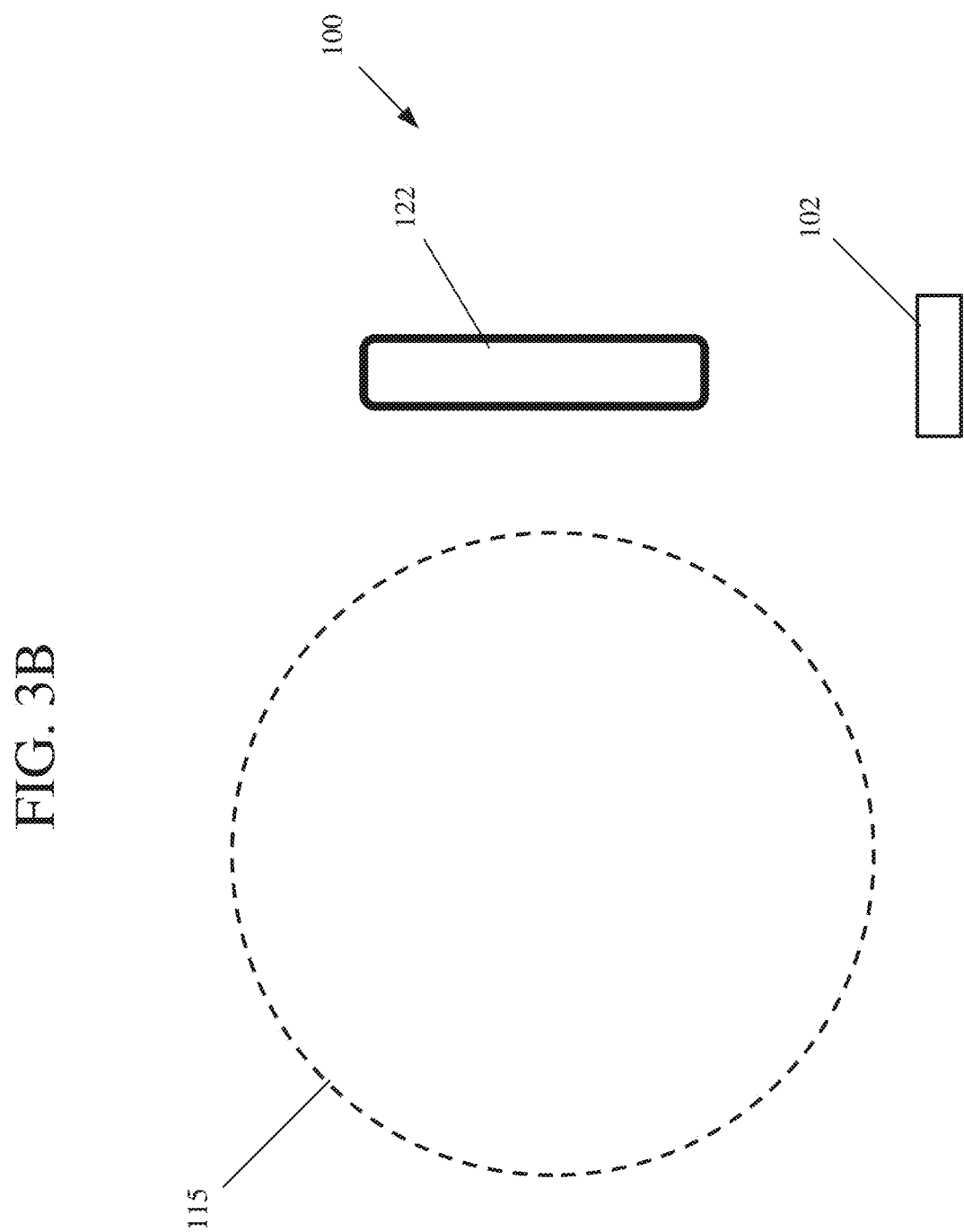

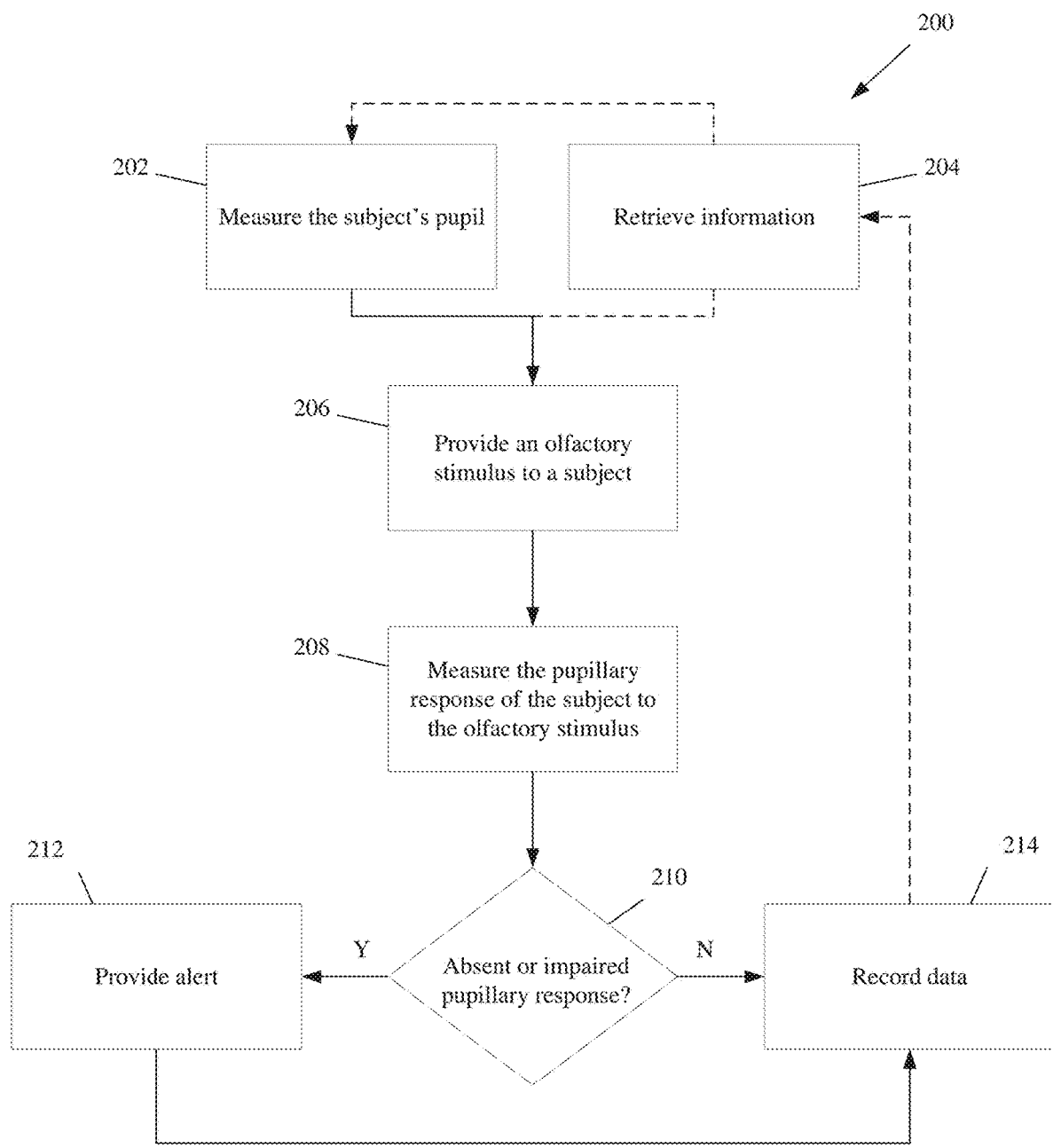

SYSTEMS AND METHODS FOR SCREENING SUBJECTS BASED ON PUPILLARY RESPONSE TO OLFACTORY STIMULATION

BACKGROUND

Transitory decrease (hyposmia) or loss (anosmia) of sense of smell and transitory decrease (hypogeusia) or loss (ageusia) of sense of taste are two symptoms that can differentiate COVID-19 from other respiratory and influenza-like infections. These symptoms have been characterized as some of, or even, the earliest and most commonly reported features of COVID-19 and may be better indicators of the presence of the disease than other signs and symptoms (such as fever). Research has shown that individuals who tested positive for COVID-19 were 27.1 times more likely to experience anosmia and/or dysgeusia than individuals who tested negative for the disease, but only approximately 2.0 to 2.6 times more likely to have fever or chills, cough, respiratory difficulty, myalgia/arthralgia, and other symptoms associated with COVID-19. Further, research has demonstrated that a clinically significant percentage of people who test positive for COVID-19 report anosmia (up to 87%) and an even higher percentage are diagnosed with anosmia when tested using objective methods that measure the function of smell. Therefore, impairment of sense of smell or taste is a useful indicator that an individual should undergo medical evaluation for COVID-19, because it is both more highly predictive than other symptoms and a more unique symptom (one of the first symptoms, or even the only symptom, in approximately 25% of cases) than many other symptoms of COVID-19 (e.g., fever, chills, or cough).

Further, it is known that activation of smell sense receptors results in a change in nervous system tone, resulting in pupillary dilation. Pupillary dilation in response to a scent is a well-known scientifically employed measure of sense of smell. Therefore, measuring an individual's pupillary response to an olfactory stimulus can be used to determine whether the individual could be suffering from hyposmia or anosmia.

A system that could screen for COVID-19 in an accurate, reliable and quantitative manner based on individuals' responses (or lack thereof) to olfactory stimuli would benefit the individuals themselves and additionally provide a significant public health benefit. Additionally, a variety of other conditions, such as multiple sclerosis, Alzheimer's disease and other forms of dementia, are associated with variations in sense of smell. Therefore, such a system could also be used to screen for these types of conditions.

SUMMARY

There are provided systems and methods for screening subjects for changes in response to a provided stimulus, such as an olfactory stimulus.

In some embodiments, there is provided a computer-implemented method for screening a subject for a response to an olfactory stimulus as an indication for a condition, the method comprising: providing, via a scent dispenser, the olfactory stimulus to the subject; measuring, via a detector, a pupillary response of the subject to the olfactory stimulus; comparing the measured pupillary response to a reference; determining whether the subject demonstrates a diminished or an absent response to the olfactory stimulus according to whether the measured pupillary response differs from the reference by a threshold; and providing an alert according to whether the subject has the diminished or the absent response to the olfactory stimulus, wherein the alert comprises an intervention associated with the condition.

In some embodiments, the condition comprises COVID-19.

In some embodiments, the measured pupillary response comprises a change in size of a pupil of the subject.

In some embodiments, the method further comprises determining whether there is a secondary factor associated with the subject that could affect the measured pupillary response, wherein determining whether the subject demonstrates the diminished or the absent response to the olfactory stimulus is further based on the determined secondary factor.

In some embodiments, determining whether there is the secondary factor associated with the subject comprises: determining, via the detector, an amount of environmental light associated with the subject.

In some embodiments, the intervention comprises at least one of a recommendation to take a diagnostic test or a recommendation to seek medical evaluation.

In some embodiments, the diagnostic test recommended could be a COVID-19 diagnostic test.

In some embodiments, the reference comprises a default value.

In some embodiments, the reference comprises a characterized pupillary response by the subject to the olfactory stimulus.

In some embodiments, the reference comprises a characterized pupillary response of a population of individuals to the olfactory stimulus.

In some embodiments, the olfactory stimulus comprises a peppermint scent.

In some embodiments, the detector is associated with a mobile device.

In some embodiments, the alert comprises a push notification.

In some embodiments, there is provided a system for screening a subject for a response to an olfactory stimulus as an indication for a condition, the system comprising: a scent dispenser configured to store an olfactory stimulus; and a mobile device comprising: a detector, a processor, and a memory coupled to the processor, the memory storing instructions that, when executed by the processor, cause the processor to: cause the scent dispenser to provide an olfactory stimulus to the subject, measure, via the detector, a pupillary response of the subject to the olfactory stimulus, compare the measured pupillary response to a reference, determine whether the subject demonstrates a diminished or an absent response to the olfactory stimulus according to whether the measured pupillary response differs from the reference by a threshold, and provide an alert according to whether the subject has the diminished or the absent response to the olfactory stimulus, wherein the alert comprises an intervention associated with the condition.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings:

FIG. 1 illustrates a diagram of a screening system, in accordance with an embodiment.

FIG. 3A illustrates a front view of a second embodiment of the screening system of FIG. 1.

FIG. 3B illustrates a side view of the second embodiment of the screening system of FIG. 3A.

FIG. 5 illustrates a flow diagram of a process for screening a subject for a condition via an olfactory stimulus, in accordance with an embodiment.

DETAILED DESCRIPTION

Figure 2A:
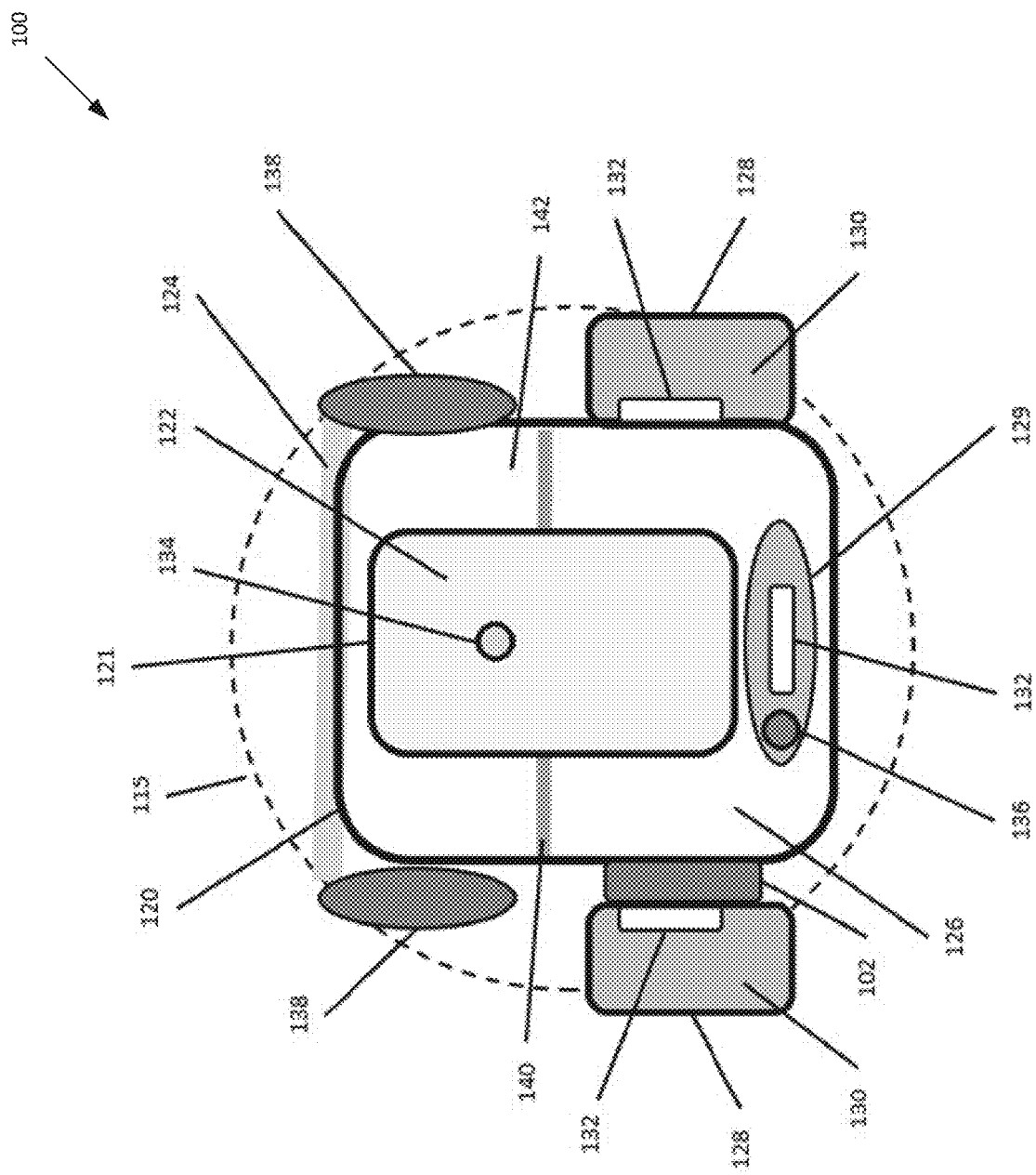
FIG. 2A illustrates a front view of a first embodiment of the screening system of FIG. 1.

As used herein, "COVID-19" means the infectious disease caused by the SARS-CoV-2 virus.

As used herein, a "subject" refers to a human individual.

Generally described herein are various systems and processes for screening subjects for degree of response by providing a subject with a stimulus (e.g., an olfactory stimulus) and measuring a response (e.g., pupillary response) by the subject to the stimulus. In one embodiment, the measured response could include an autonomic response by the subject to the stimulus. These systems and methods can be used for screening subjects for findings that indicate reduction or absence of subjects' responses to the stimulus. The changes in response to screening could be used, for example, to trigger recommendation for medical evaluation for conditions which may include COVID-19, multiple sclerosis, Alzheimer's disease, or other forms of dementia. Because hyposmia and/or anosmia are associated with each of these conditions, the systems and processes described herein can be used to screen a subject by assessing the subject's response to an olfactory stimulus. Degree of response during screening may be used to prompt the subject to seek medical evaluation, possible further testing, or take a variety of other actions (e.g., self-quarantine or isolation). Accordingly, the systems and processes described herein can be used to accurately, reliably, qualitatively, and quantitatively screen individuals for abnormal responses that may indicate need for medical evaluation.

Systems for Screening Subjects

In one embodiment, a screening system 100 can include a scent dispenser 102 that is configured to provide an olfactory stimulus to a subject and a detector 104 (e.g., a camera, an image sensor, or another sensing and/or recording device) that is configured to sense a change in a response (e.g., pupillary response) by the subject simultaneous with or shortly after the subject has been provided the stimulus. In one embodiment, the detector 104 could be configured to capture images and/or video of the subject. The detector 104 could include standalone sensing devices or be incorporated into another device (e.g., a mobile device 122, as in the embodiment shown in FIGS. 2A and 2B) or system. Further, in some embodiments, the detector 104 could include one sensor or a set of sensors (i.e., a sensor assembly). The screening system 100 can be configured to execute various processes, such as those described below, to screen individuals based on their response or responses to stimuli provided by the screening system. In one embodiment, the screening system 100 can further include a processor 106 coupled to a memory 108 for storing data, including logic or instructions embodying processes to be executed by the processor.

The scent dispenser 102 can be configured to store and deliver a dose of one or more scents or olfactory stimuli to the subject. The scent dispenser 102 can be communicably coupled to the processor 106 such that the scent dispenser 102 can be controlled or triggered thereby. In one embodiment, the olfactory stimulus could include selected scents and/or scent-producing compounds or inhalants (e.g., peppermint scent).

The detector 104 can be configured to capture images or video of a subject in sufficient detail such that the subject's pupillary response to the olfactory stimulus can be measured. In other words, the detector 104 can be configured to capture images or video in a sufficiently high resolution and with sufficient clarity such that image processing algorithms can identify the subject's pupils and measure changes associated therewith. In various embodiments, the pupillary response measured by the detector 104 could include a change in the size (e.g., diameter or area) of the subject's pupil or pupils, timing information (e.g., hesitancy or delay in the pupil's movement), and other pupillary parameters. For example, the detector 104 could be used to take a first measurement of the size of the subject's pupil or pupils and take a second measurement of the size of the subject's pupil or pupils after the subject has been provided the olfactory stimulus. In this example, the pupillary response could include the difference between the measurements of the subject's pupillary size. As another example, the detector 104 could be configured to measure the hesitancy or delay in the change in size of the subject's pupil or pupils after the subject was provided the olfactory stimulus. In this example, the pupillary response could include the time delay between when the olfactory stimulus is provided and when the subject's pupil or pupils begin to change in size.

The screening system 100 can be embodied as a variety of different objects, devices, or systems. In one embodiment, the screening system 100 could include a mobile device (e.g., a smartphone) and the processes executed thereby could include an app. In this embodiment, the screening system 100 could be beneficial by allowing individuals to self-screen for a particular condition or set of conditions using their own mobile device. In some embodiments, the scent dispenser 102 could be embodied as an accessory or dongle that is connectable (either wirelessly or via a wired connection) or attachable to the mobile device. In other embodiments, the scent dispenser 102 could be a device that is manually operated by the user. Further, the detector 104 could include the onboard camera of the mobile device. Other embodiments could be suitable for screening individuals for entry to potentially crowded locations (e.g., schools, airports, or stadia). In one such embodiment, the screening system 100 could include a kiosk or station that includes the scent dispenser 102 and the detector 104. In this embodiment, the screening system 100 could be beneficial by allowing individuals to be screened for potential abnormalities (e.g., such as those associated with COVID-19) prior to being permitted entry into a location. An abnormal response could be used as one of the tools to decide whether individuals should be permitted access to a venue, or require additional screening, thereby potentially avoiding significant adverse consequences (e.g., disease transmission events).

The screening system 100 can further include or be communicably connected to a database 110. In one embodiment, the database 110 could be stored locally (i.e., in the memory 108). In another embodiment, the database 110 could be remote from the screening system 100. In this embodiment, the database 110 could be stored in a cloud computing storage system (e.g., Amazon Web Services), a remote server, and other such remote systems. The database 110 can be configured to store information including user parameters and settings, such as the user's preferred and previously calibrated scents. The user parameters could be embodied as a user profile, for example. The user parameters could include previously recorded values or measurements associated with the response measured by the screening system 100. The recorded parameters can be used to define a characterized or default response by the subject to the stimulus, which can in turn be used by the screening system 100 to determine when the subject's measured response deviates from this characterized or default response by the subject. Accordingly, the screening system 100 can determine when there has been a change in the patient's response to the stimulus, which could indicate that the patient has a condition that is screened by the screening system 100. The characterized or default response could be used to define various thresholds or ranges that could be used to determine whether the subject has passed or failed the screening. Accordingly, the screening system 100 can be configured to take measurements (e.g., via the detector 104) associated with the subject's response to the stimulus, retrieve a user profile associated with the subject (e.g., from the database 110), and determine whether the subject has passed or failed the screening based on a comparison between the measurements of the response and the user profile parameters. For example, the screening system 100 can be configured to administer a dose of an olfactory stimulus to the subject via the scent dispenser 102 and measure the resulting pupillary response (e.g., pupil size). If no dilation of the subject's pupils occurs (e.g., as compared to the stored profile associated with the subject or a universal characterized response), then the subject may be suffering from anosmia. Further, less pupil dilation than normal may indicate hyposmia. In either of these cases, the screening system 100 could prompt the subject regarding the need for medical evaluation (such as a physician checkup and/or testing including COVID-19 test), and that the individual take corresponding appropriate precautions (e.g., self-quarantine or isolation).

The screening system 100 can further be configured to account for various secondary factors and be calibrated for each individual subject. For example, the screening system 100 may need to be calibrated to determine the degree of dilation by the subject that exceeds a threshold so that the screening system can distinguish between anosmia and lesser abnormalities, such as from partial nasal blockage (e.g., nasal congestion) blunting of the sense of smell.

In one embodiment, the screening system 100 can be configured to determine the amount of light in the patient's environment (e.g., via the detector 104) and, accordingly, account for the amount of light employed to determine response to the screening. The amount of ambient or environmental light can be an important factor because one of the principal reasons for the contraction and dilation of the pupils is to control the amount of light entering the interior of the eye. Thus, the amount of light present during a screening test can have a significant effect on the amount of pupil dilation in response to a dose of scent. In particular, a brightly lit ambient environment would decrease the pupil opening and, because the pupil is constricted, it may not dilate normally in response to an olfactory stimulus. Conversely, in a dimly lit ambient environment, the pupil may already be dilated, or the screening system 100 may be unable to detect the degree of dilation in response to a dose of the olfactory stimulus. Thus, in some embodiments, the screening system 100 can measure the amount of environmental light and recommend or effect adjustments for appropriate screening, such as blocking environmental light. In some embodiments, the screening system 100 can additionally be configured to control the amount of light in the test environment, such as by activating or controlling lights in the test environment.

In one embodiment, the screening system 100 could be configured to measure the subject's pupillary response to various levels and spectra of light during a calibration process for the subject. Because each individual can react differently to various levels and spectra of light, a particular subject's response to these conditions could provide a basis for deciding the optimal level of light for screening each subject. Similarly, the screening system 100 could be configured to determine an optimal color spectrum of light for the subject and/or the particular hardware of the detector (e.g., the camera 104).

In one embodiment, the screening system 100 could be configured to determine whether the subject is unable to respond to light and/or olfactory stimuli. For example, the screening system 100 could automatically detect the presence of various indicators (e.g., cataracts), retrieve patient information (e.g., electronic medical records) from a database, or prompt the user to enter such information. This information is important because some indicators (such as cataracts) affect pupillary response. Pupillary responses may be affected in different ways by different indicators. Thus, in some embodiments, the screening system 100 could be configured to detect and differentiate among such indicators. The screening system 100 could be configured to incorporate the presence of these indicators into the determination of the likelihood that the decrease or lack of pupillary change is related to anosmia. In addition, the screening system 100 could be configured to recommend additional screenings in the event that more determinations or more time would be advantageous in achieving a successful screening.

In one embodiment, the screening system 100 could be configured to detect scents in the subject's environment. For example, the screening system 100 could include one or more scent sensors (i.e., electronic noses). The presence of environmental scents could be important because environmental scents may interfere with pupil dilation in response to an olfactory stimulus. In particular, some scents, especially very strong scents, may trigger responses that could override the subject's normal pupillary dilation response. Accordingly, environmental scents could generate both false positive and false negative test results. In some embodiments, the screening system 100 could be configured to control the level of scents in the test environment. For example, the screening system 100 could include an air filtering system. In some embodiments, the screening system 100 could be configured to measure the presence, intensity, and/or types of scents in the subject's environment. In these embodiments, the screening system 100 could evaluate whether the environment is appropriate for screening, recommend or adjust the screening environment conditions, and/or reschedule the subject for a retest, for example.

In some embodiments, the screening system 100 could be configured to account for a variety of other events or subject-specific or environmental conditions. For example, the screening system 100 could be configured to detect when the user was startled at the time of the test (e.g., due to a loud sound or bright flash) and adjust environmental conditions or recommend that the subject be retested, for example. In one implementation, the screening system 100 could ask the subject one or more questions, such as "Are you currently suffering from nasal congestion?", prior to beginning the screening test and act accordingly based on the subject's responses (e.g., recommending that the test be postponed).

All of the various data associated with the subject that are discussed above, such as the subject's amount of pupil dilation at various lighting levels, the subject's response to spectra of light, and so on, could be stored in a user profile associated with the subject. As discussed above, this data can be stored by and/or retrieved by the screening system 100 at the time of the screening test to assist in the determination of positive or negative results of screening.

Figure 2B:
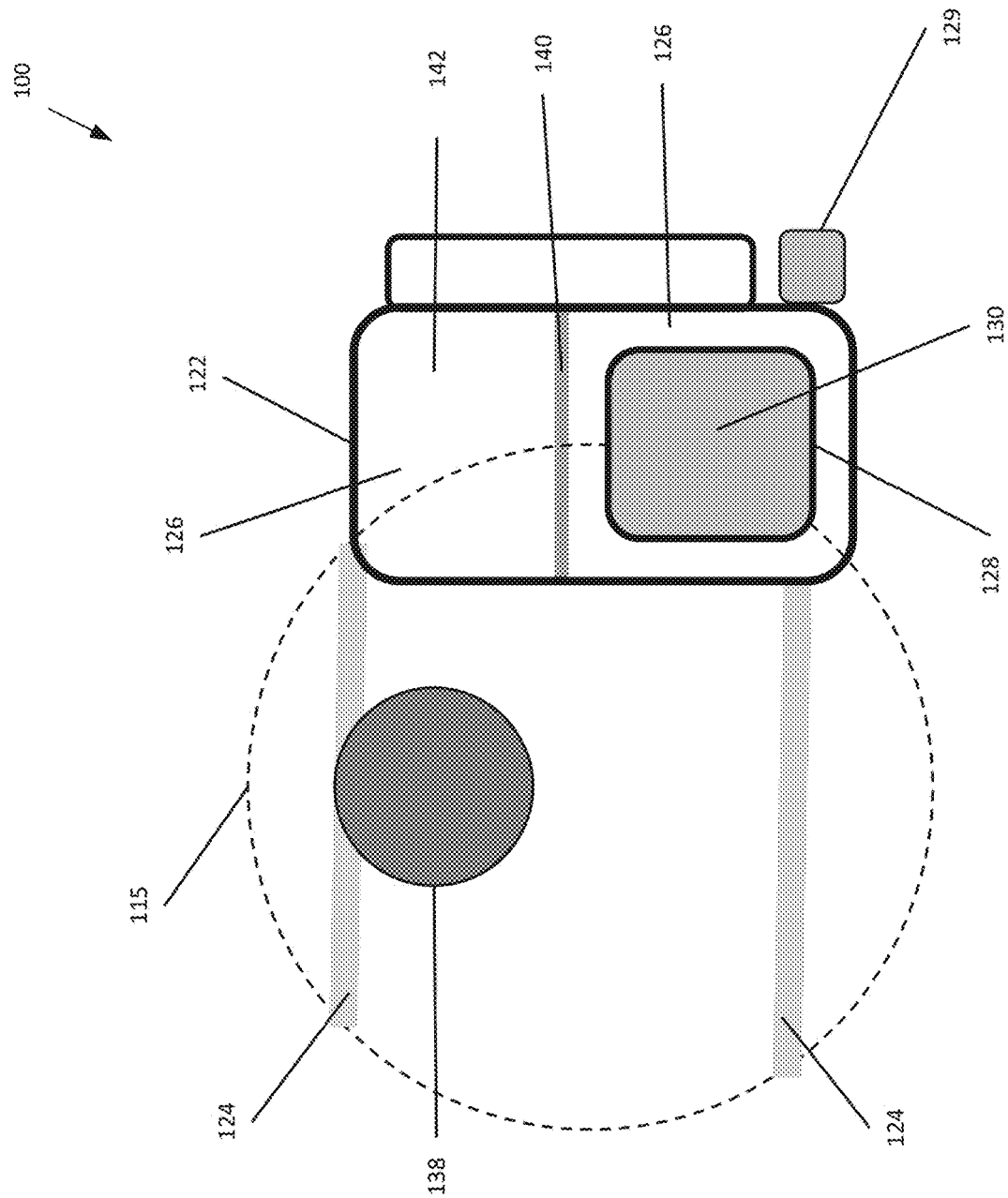
FIG. 2B illustrates a side view of the first embodiment of the screening system of FIG. 2A.

One embodiment for the screening system 100 is shown in FIGS. 2A and 2B. In this embodiment, the screening system 100 could include a headpiece 120 that can be worn on the head 115 of the subject. In the illustrated embodiment, the headpiece 120 includes a holder 121 that is configured to hold a mobile device 122 (e.g., a smartphone or another smart device) that includes a detector 104 (e.g., a camera). The holder 121 can be configured to hold the mobile device 122 such that the detector 104 is oriented towards the subject's face when the headpiece 120 is worn by the subject. The mobile device 122 executing the app can be used to guide the subject through the screening steps with audio, images, text, or combinations thereof. Accordingly, in one implementation, users could place their mobile device 122 in the holder 121 and the mobile device can in turn execute an app stored thereon that performs the screening test, as described herein. In another embodiment, the detector 104 could be integral to the headpiece 120. The headpiece 120 can include one or more straps 124 or other securement devices for securing the headpiece to the subject's head 115 and keep the mobile device 122 in a fixed relationship to the subject's face.

In one embodiment, the headpiece 120 could define an enclosed air chamber 126 that is configured to provide a fixed environment suitable for the screening test for the subject. The headpiece 120 could further include an air inlet 128 (which can further include a filter 130, such as a P100 filter) and a corresponding outlet 129 for allowing the subject to exhale. The headpiece 120 can further include the scent dispenser 102 that delivers an olfactory stimulus to the subject. In one embodiment, the olfactory stimulus delivered by the scent dispenser 102 could be selected based upon its ability to produce the desired response. System calibration could include testing of different scents and scent intensities to determine the most appropriate for a particular subject. The scent dispenser 102 could be activated by the subject or automatically by the screening system 100 (e.g., by the software app running on a mobile device 122). In embodiments where the screening system 100 activates the scent dispenser 102, the subject may not be aware of when the scent is provided. This could be advantageous because having the scent provided without the user's knowledge could prevent anticipatory changes from confounding findings of response.

In various embodiments, the headpiece 120 can include various additional components to assist in the administration and assessment of the screening test. For example, the headpiece 120 could further include one or more air flow meters 132 that are configured to measure the intake and outflow of air. In some embodiments, the amount of airflow through the headpiece 120 may be used as a secondary factor by the screening system 100 to assist in the assessment of the subject's response. In some embodiments, the headpiece 120 may include a focus dot 134 that can be used to focus the subject's gaze and attention during the screening procedure. In some embodiments, the headpiece 120 may include a scent measuring device 136 that is configured to measure the intensity and types of scents in the air chamber 126 and/or the subject's environment. As noted above, environmental scents can affect the results of the screening test, so the screening system 100 can be configured to identify environmental scents via the scent measuring device 136 and use this information in the assessment of the subject during the screening test, for example.

In still other embodiments, the headpiece 120 could include earphones 138 to control or reduce environmental noise and direct sounds from the mobile device 122 or sensor to the subject. As yet another example, the headpiece 120 could include an air dam 140 to separate the air chamber 126 from the eye chamber 142 so that air flow and scents do not interfere with the pupillary measurements. Such embodiments can be beneficial because they provide a controlled environment for the performance of the screening test, which can increase reliability of the results.

Another embodiment of the screening system 100 is shown in FIGS. 3A and 3B. In this embodiment, rather than using the headpiece assembly described above with respect to FIGS. 2A and 2B, the subject could instead hold their mobile device 122 (or a detector 104) in close proximity to his or her face (or rest the mobile device 122 in an appropriate location) with the scent dispenser 102 in close proximity. In this embodiment, the relationship between the subject's head 115 and the mobile device 122 is not fixed, so the mobile device (or the software app executed thereby) can therefore be configured to compensate for motion of the subject relative to the mobile device. Such an embodiment can be beneficial because of its ease of use. In particular, such an embodiment does not require a substantial number of components or for the subject to wear a head assembly or otherwise be within a fixed environment.

Figure 4A:
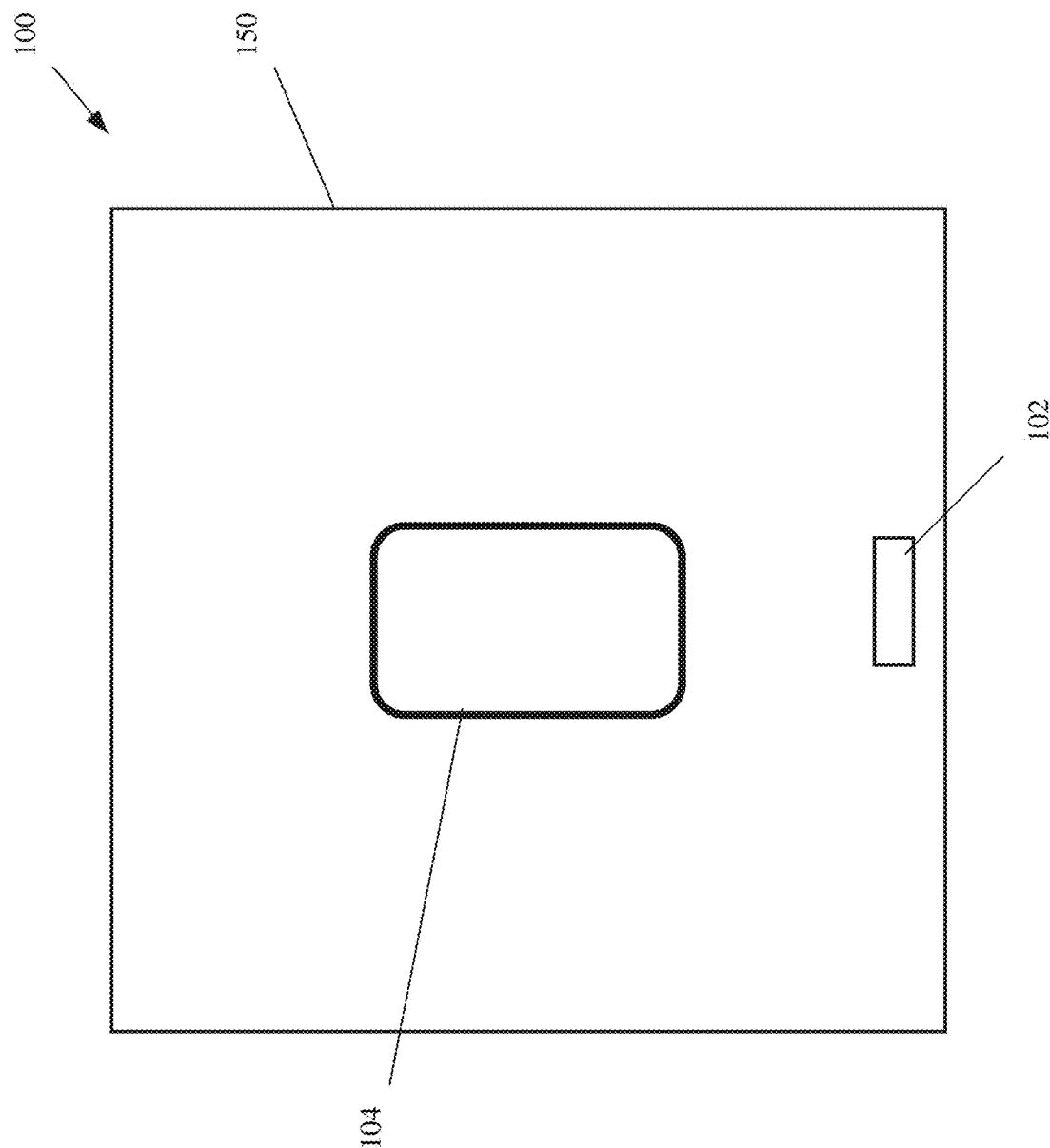
FIG. 4A illustrates a front view of a third embodiment of the screening system of FIG. 1.
Figure 4B:
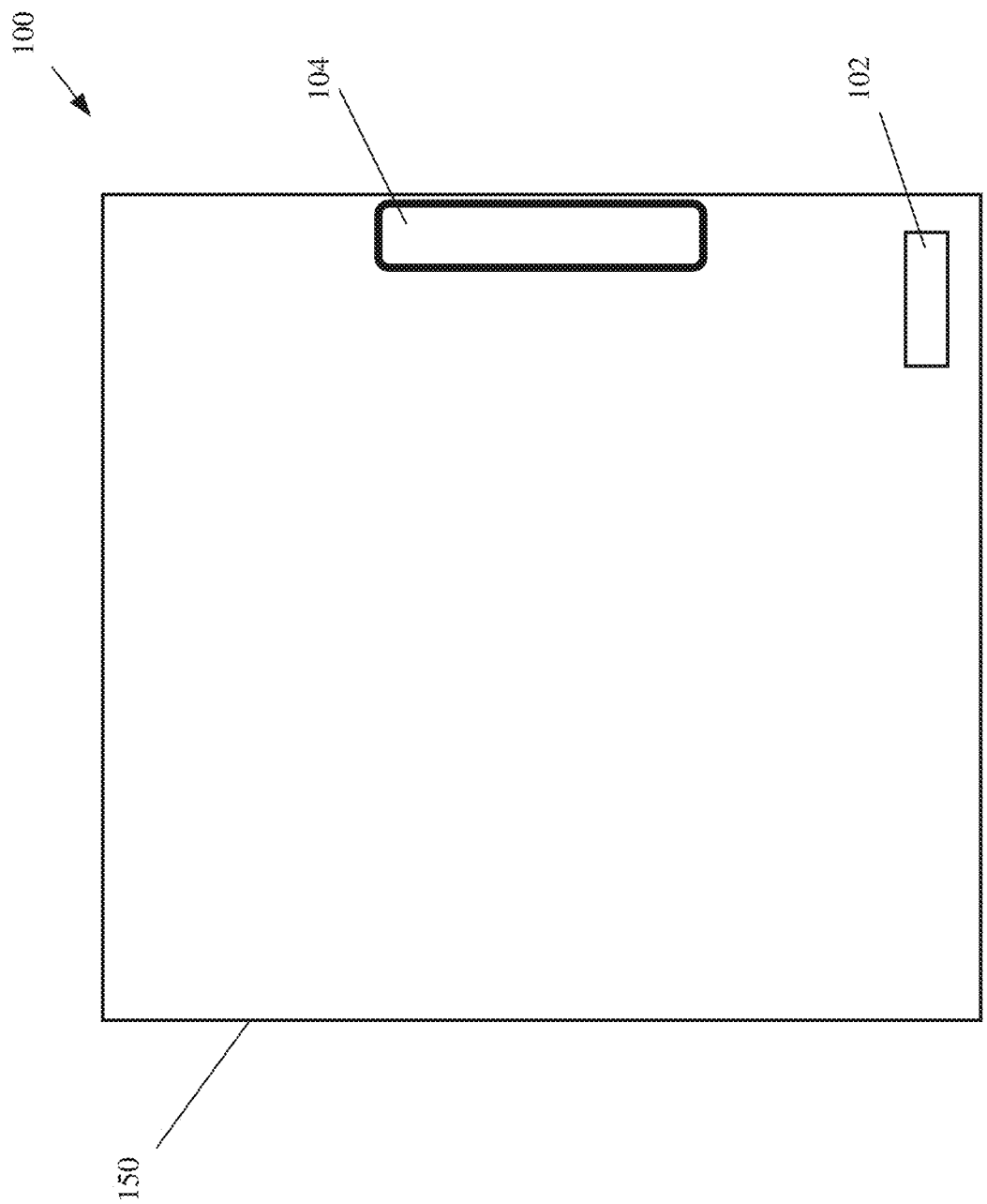
FIG. 4B illustrates a side view of the third embodiment of the screening system of FIG. 4A.

Yet another embodiment of the screening system 100 is shown in FIGS. 4A and 4B. In this embodiment, the screening system 100 is embodied as a high-throughput, touch-free system that could be suitable for screening at airports, stadia, and so on. In particular, this embodiment of the screening system 100 can include an enclosure 150 into which the subject can enter. The enclosure 150 could be an enclosure that is environmentally controlled, for example. The enclosure 150 could include a complete or partial enclosure. (e.g., from the waist up). In such an embodiment, the subject enters the enclosure 150 and faces the detector 104. As noted above, the detector 104 could include a camera or an image sensor, for example. The detector 104 could be positioned on a wall of the enclosure at a height suitable for visualizing individuals' faces, for example, or at adjustable heights to optimize the relationship to the face. The detector 104 could provide appropriate instructions to the subject (e.g., where to stand), what information to provide to the screening system 100 (e.g., whether the subject has any relevant information that may inform results of screening), or when to exit. The detector 104 could include a smart device or a specialized sensor apparatus. The scent dispenser 102 could be integral to the enclosure 150 and/or the detector 104 or otherwise located within the enclosure 150. In one embodiment, the scent dispenser 102 could be communicably coupled to the detector 104 such that it is controlled thereby (e.g., to release the olfactory stimulus).

Screening Based on Olfactory Stimuli

In one embodiment, systems, such as the system 100 described above, can be configured to execute various processes for screening subjects for certain responses based on olfactory stimuli. One example of such a process 200 is shown in FIG. 5. In the following discussion of the process 200, reference should also be made to FIG. 1. In one embodiment, the process 200 can be embodied as instructions stored in a memory 108 that, when executed by a processor 106, cause the screening system 100 to perform the process. In various embodiments, the process 200 can be embodied as software, hardware, firmware, and various combinations thereof.

Accordingly, the screening system 100 executing the process 200 can measure 202 the subject's pupil. For example, the screening system 100 can measure 202 the size of the subject's pupil. In one embodiment, the screening system 100 can take the measurement via the detector 104. Prior to, contemporaneous with, or after measuring 202 the subject's pupil, the screening system 100 can retrieve 204 information associated with the subject, the subject's ambient environment, or other testing parameters that could be used to control aspects of the measurement 202 performed by the screening system (e.g., shutter speed of a camera being used to measure the subject's pupillary response). In various embodiments, the retrieved 204 information could include a reference against which the subject's measured pupillary response is compared. In one embodiment, the reference could include a default value, such as a preprogrammed value associated with the given olfactory stimulus. In another embodiment, the reference could include a characterized pupillary response by the subject to the olfactory stimulus. For example, the screening system 100 could be programmed to store a number of pupillary response measurements by the subject and characterize the tusual range of pupillary responses for the subject for the given olfactory stimulus. In yet another embodiment, the reference could include characterized pupillary responses of a population of individuals to the olfactory stimulus. In this embodiment, data from a population of users could be pooled and analyzed to characterize the usual range of pupillary responses for particular stimuli.

In various embodiments, the reference could be stored in a profile associated with the subject. As discussed above, the subject's user profile can include one or more parameters or references associated with the subject's pupillary response, such as characterized pupillary response values for different olfactory stimuli that have been pre-characterized for the subject (e.g., during a calibration process performed by the screening system 100). In various embodiments, the reference could be stored in a database 110 that that screening system 100 is associated with or communicably coupled to. In these embodiments, the screening system 100 could be programmed to retrieve the reference from the database 110.

Accordingly, the screening system 100 can provide 206 an olfactory stimulus to a subject via the scent dispenser 102. As noted above, the olfactory stimulus could include a variety of different scents or compositions. Further, the screening system 100 can measure 208 the pupillary response of the subject to the provided olfactory stimulus via the detector 104.

Accordingly, the screening system 100 can determine 210 whether the subject has a absent or diminished pupillary response to the olfactory stimulus. In one embodiment, the screening system 100 can compare the measured pupillary response to a reference for the subject (e.g., which could be included in the retrieved 204 information described above) and determine whether the measured pupillary response differs from the retrieved reference. In one embodiment, the screening system 100 may determine whether the measured pupillary response differs from the reference by a threshold. For example, in an embodiment where the pupillary response includes the size of the subject's pupil, the threshold could be based on the usual difference between the subject's pre-stimulus and the post-stimulus pupillary sizes. In another embodiment, the screening system 100 could determine whether the measured pupillary response falls outside of a particular range of values associated with the pupillary response profile. If the measured pupillary response does differ from the reference, the screening system 100 can provide 212 an alert to the subject. As noted above, if the measured pupillary response differs from the pupillary response profile, the screening system 100 could recommend medical evaluation and/or testing. In various embodiments, the results of screening could be used to prompt medical evaluation (for COVID-19, multiple sclerosis, Alzheimer's disease, or other forms of dementia, for example). The alert could include a push notification provided via a mobile device, a text message, an email, a popup message, and so on. The alert could provide additional recommendations, such as that the user should seek medical evaluation and advice regarding additional testing or whether to take precautionary measures (e.g., self-quarantine or isolation). If the measured pupillary response does not differ from the pupillary response profile, the screening system 100 could record 214 the data associated with the screening test. In one embodiment, the screening system 100 could likewise record the data associated with the screening test when the measured pupillary response differs from the reference. In one embodiment, the screening system 100 could further add the recorded 214 data to a database, such as the database from which the information is retrieved 204 as described above.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The functions and process steps herein may be performed automatically or wholly or partially in response to user command. An activity (including a step) performed automatically is performed in response to one or more executable instructions or device operation without user direct initiation of the activity.

What is claimed is:

1. A computer-implemented method for screening a subject for a response to an olfactory stimulus as an indication for COVID-19, the method comprising:
    providing, via a scent dispenser, the olfactory stimulus to the subject;
    measuring, via a detector of a mobile device, a pupillary response of the subject to the olfactory stimulus;
    comparing, by a processor of the mobile device, the measured pupillary response to a reference;
    determining, by the processor, whether the subject demonstrates a diminished or an absent response to the olfactory stimulus according to whether the measured pupillary response differs from the reference by a threshold; and
    providing, by the processor, an alert according to whether the subject has the diminished or the absent response to the olfactory stimulus, wherein the alert comprises an intervention associated with COVID-19.

2. The computer-implemented method of claim 1, wherein the measured pupillary response comprises a change in size of a pupil of the subject.

3. The computer-implemented method of claim 1, further comprising:
    determining whether there is a secondary factor associated with the subject that could affect the measured pupillary response, wherein determining whether the subject demonstrates the diminished or the absent response to the olfactory stimulus is further based on the determined secondary factor.

4. The computer-implemented method of claim 3, wherein determining whether there is the secondary factor associated with the subject comprises:

determining, via the detector, an amount of environmental light associated with the subject.

5. The computer-implemented method of claim 1, wherein the intervention comprises at least one of a recommendation to take a COVID-19 diagnostic test or a recommendation to seek medical evaluation.

6. The computer-implemented method of claim 1, wherein the reference comprises a default value.

7. The computer-implemented method of claim 1, wherein the reference comprises a characterized pupillary response by the subject to the olfactory stimulus.

8. The computer-implemented method of claim 1, wherein the reference comprises a characterized pupillary response of a population of individuals to the olfactory stimulus.

9. The computer-implemented method of claim 1, wherein the olfactory stimulus comprises a peppermint scent.

10. A system for screening a subject for a response to an olfactory stimulus as an indication for COVID-19, the system comprising:
a scent dispenser configured to store an olfactory stimulus; and
a mobile device comprising:
a detector,
a processor, and
a memory coupled to the processor, the memory storing instructions that, when executed by the processor, cause the processor to:
cause the scent dispenser to provide an olfactory stimulus to the subject,
measure, via the detector, a pupillary response of the subject to the olfactory stimulus,
compare the measured pupillary response to a reference,
determine whether the subject demonstrates a diminished or an absent response to the olfactory stimulus according to whether the measured pupillary response differs from the reference by a threshold, and
provide an alert according to whether the subject has the diminished or the absent response to the olfactory stimulus, wherein the alert comprises an intervention associated with COVID-19.

11. The system of claim 10, wherein the pupillary response comprises a change in size of a pupil of the subject.

12. The system of claim 10, wherein the memory further stores instructions that, when executed by the processor, cause the processor to:
determine whether there is a secondary factor associated with the subject that could affect the measured pupillary response, wherein determining whether the subject demonstrates the diminished or the absent response to the olfactory stimulus is further based on the determined secondary factor.

13. The system of claim 12, wherein the secondary factor comprises an amount of environmental light associated with the subject as determined via the detector.

14. The system of claim 10, wherein the intervention comprises at least one of a recommendation to take a COVID-19 diagnostic test or a recommendation to seek medical evaluation.

15. The system of claim 10, wherein the alert comprises a push notification.

16. The system of claim 10, wherein the reference comprises a default value.

17. The system of claim 10, wherein the reference comprises a characterized pupillary response by the subject to the olfactory stimulus.

18. The system of claim 10, wherein the reference comprises a characterized pupillary response of a population of individuals to the olfactory stimulus.

19. The system of claim 10, wherein the olfactory stimulus comprises a peppermint scent.

* * * * *